(12) United States Patent
Kurahashi

(10) Patent No.: US 8,068,237 B2
(45) Date of Patent: Nov. 29, 2011

(54) SHEET TYPE DETECTION DEVICE THAT DETERMINES THICKNESS AND SURFACE ROUGHNESS OF A SHEET

(75) Inventor: Masahiro Kurahashi, Suzhou (CN)

(73) Assignee: Canon Kabushiki Kaisha, Tokyo (JP)

( * ) Notice: Subject to any disclaimer, the term of this patent is extended or adjusted under 35 U.S.C. 154(b) by 987 days.

(21) Appl. No.: 11/146,561

(22) Filed: Jun. 7, 2005

(65) Prior Publication Data

US 2005/0280687 A1    Dec. 22, 2005

(30) Foreign Application Priority Data

Jun. 8, 2004  (JP) ................. 2004-170296

(51) Int. Cl.
*G06F 3/12* (2006.01)
(52) U.S. Cl. ......................................... 358/1.1
(58) Field of Classification Search ............ 347/139
See application file for complete search history.

(56) References Cited

U.S. PATENT DOCUMENTS

| | | | | |
|---|---|---|---|---|
| 4,773,760 A * | 9/1988 | Makkonen | ............ | 356/631 |
| 5,138,178 A * | 8/1992 | Wong et al. | ............ | 250/559.28 |
| 5,162,660 A * | 11/1992 | Popil | ............ | 250/559.01 |
| 5,774,146 A * | 6/1998 | Mizutani | ............ | 347/43 |
| 5,898,443 A * | 4/1999 | Yoshino et al. | ............ | 347/19 |
| 6,517,180 B2* | 2/2003 | Tullis et al. | ............ | 347/19 |
| 6,527,360 B2* | 3/2003 | Otsuki et al. | ............ | 347/19 |
| 2001/0008275 A1* | 7/2001 | Yanagiuchi | ............ | 250/559.4 |
| 2004/0005157 A1* | 1/2004 | Akita | ............ | 399/45 |
| 2006/0158472 A1* | 7/2006 | Endo | ............ | 347/14 |

FOREIGN PATENT DOCUMENTS

| | | |
|---|---|---|
| JP | 57-173705 | 10/1982 |
| JP | 6-348095 A | 12/1994 |
| JP | 08-018726 | 1/1996 |
| JP | 2004-109167 | 4/2004 |

\* cited by examiner

*Primary Examiner* — Benny Tieu
*Assistant Examiner* — Jeremiah Bryar

(57) ABSTRACT

A reading sensor has first and second detection regions. The first detection region has high directivity and detects a thickness of a recording sheet. The second detection region has low directivity and detects a surface roughness of the recording sheet. The material type of the recording sheet is determined based on the detected thickness and surface roughness. Based on the type of recording sheet, conditions for forming images on the recording sheet are determined.

4 Claims, 17 Drawing Sheets

FIG. 4A
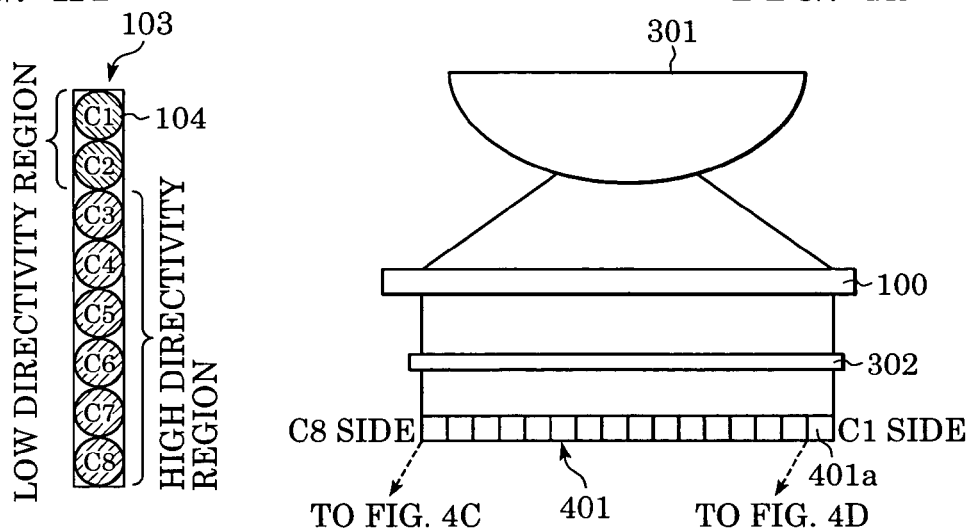
FIG. 4B
FIG. 4C  FIG. 4D
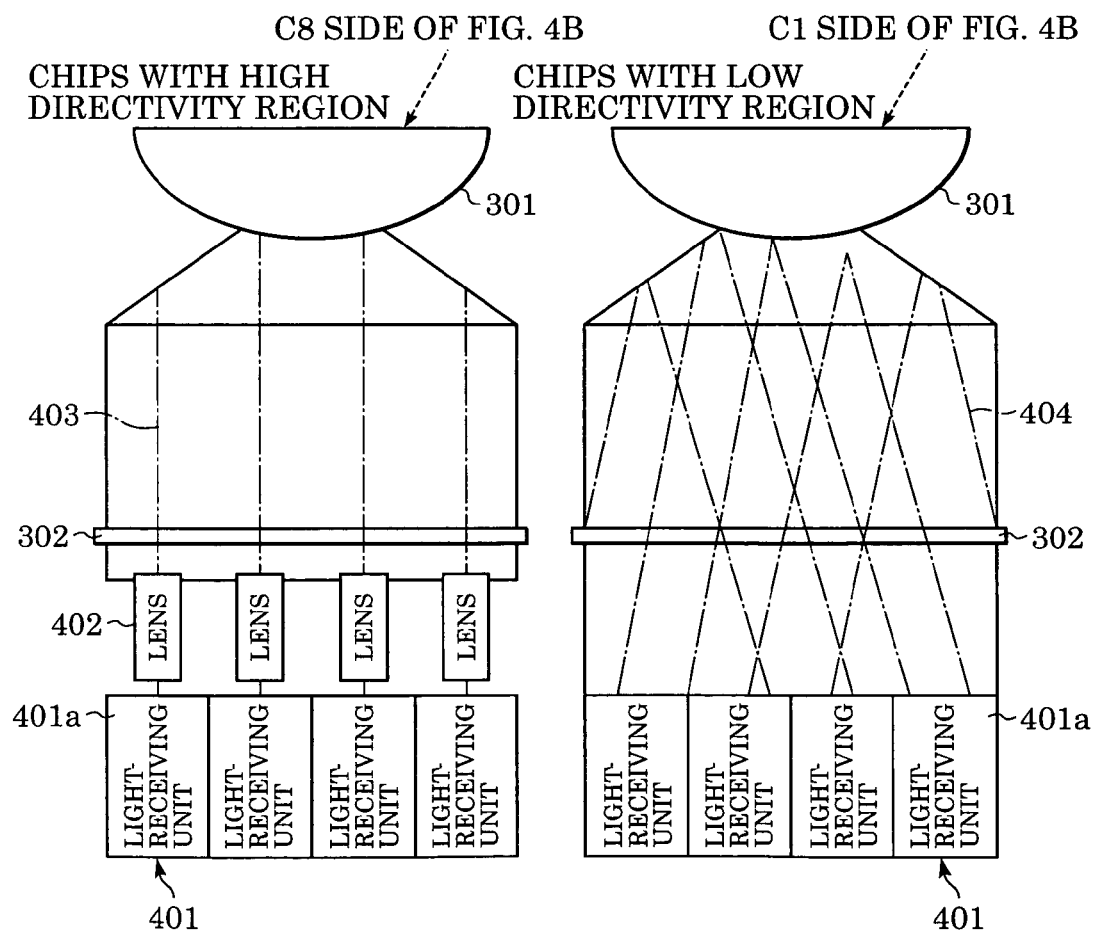

IRREGULARITIES IN LARGE AREA AT LOW
FREQUENCY: LEATHAC PAPER

IRREGULARITIES IN RELATIVELY SMALL AREA
AT HIGH FREQUENCY: EMBOSSED PAPER

SMALL IRREGULARITIES
AT HIGH FREQUENCY: SPECIAL PAPER

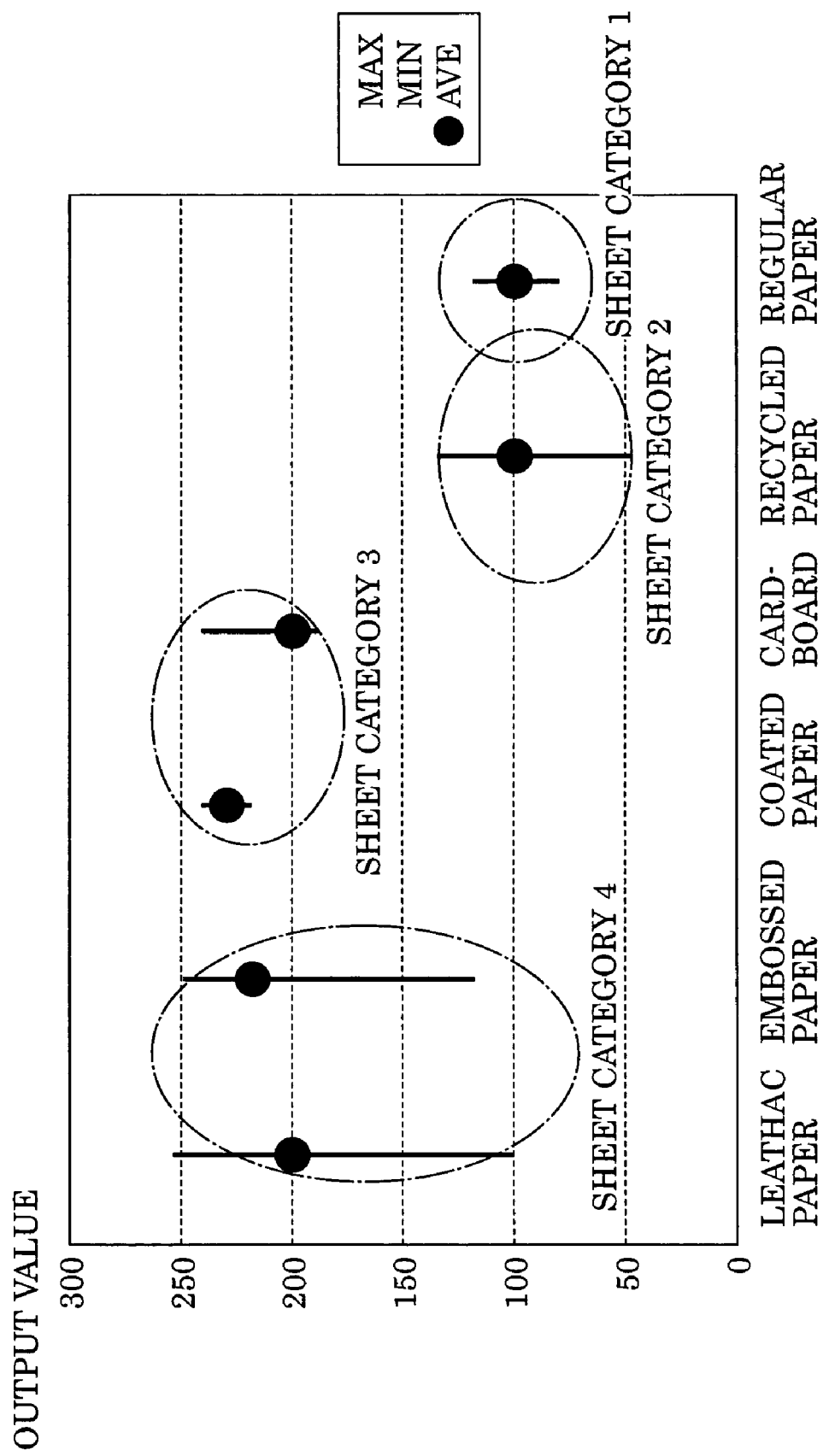

FIG. 15A

| | | ROUGHNESS [IRREGULARITY] | |
| --- | --- | --- | --- |
| | | MEDIUM/LOW | HIGH |
| THICK-NESS | MEDIUM/LOW | SHEET CATEGORY 1 | SHEET CATEGORY 2 |
| | HIGH | SHEET CATEGORY 3 | SHEET CATEGORY 4 |

FIG. 15B

| | | ROUGHNESS [IRREGULARITY] | |
| --- | --- | --- | --- |
| | | MEDIUM/LOW | HIGH |
| THICK-NESS | MEDIUM/LOW | REGULAR PAPER | RECYCLED PAPER |
| | HIGH | COATED PAPER | LEATHAC/EMBOSSED PAPER |

FIG. 15C

| | | PARAMETER | ROUGHNESS [IRREGULARITY] | |
| --- | --- | --- | --- | --- |
| | | | MEDIUM/LOW | HIGH |
| THICK-NESS | MEDIUM/LOW | TRANSFERRING | NORMAL | ENHANCED |
| | | FIXING | NORMAL | NORMAL |
| | HIGH | TRANSFERRING | NORMAL | ENHANCED |
| | | FIXING | ENHANCED | ENHANCED |

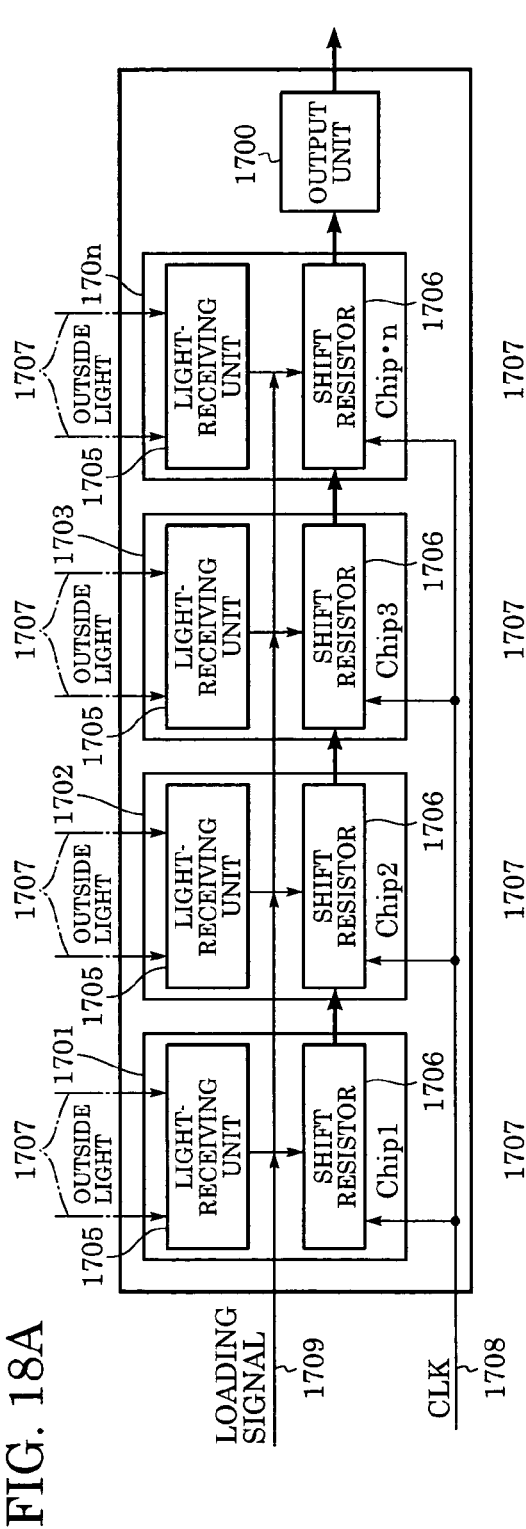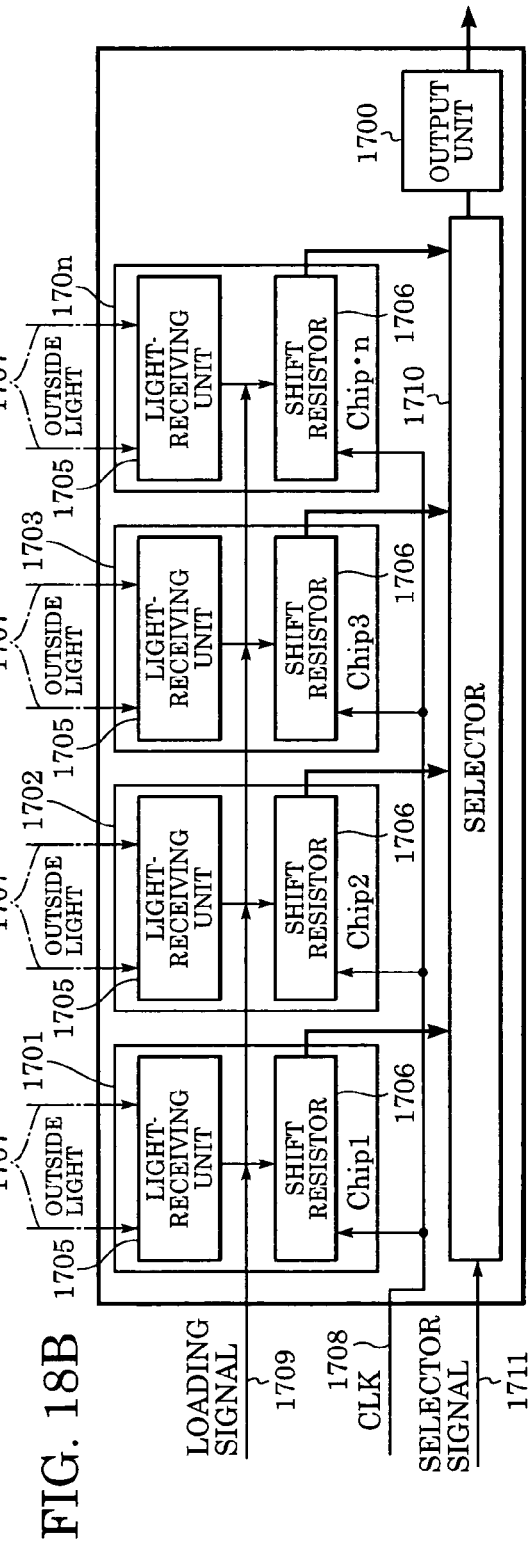

SHEET TYPE DETECTION DEVICE THAT DETERMINES THICKNESS AND SURFACE ROUGHNESS OF A SHEET

BACKGROUND OF THE INVENTION

1. Field of the Invention

The present invention relates to a sheet-type detection device for detecting the thickness and surface roughness of recording sheets made of different types of materials such as paper, nonwoven fabric, and plastic film.

2. Description of the Related Art

Known data recording devices record and output data, such as image data, at high definition. Therefore, only predetermined types of recording sheets, such as sheets of specialized paper suitable for recording data by electrography, could be used for data recording devices.

Since toner, ink, and photoreceptors have been improved, data recording on various types of commercially available multi-purpose paper has become possible.

However, to record data on various types of recording sheets, data processing parameters, data recording conditions, such as conditions for fixing and transferring an image, and mechanical control conditions, such as conditions for sheet delivery, have to be suitable for the type of sheet. In order to set suitable conditions, the various types of recording sheets have to be categorized.

The thickness of a recording sheet is inputted through a user interface of an operating unit or a hard switch. The conditions concerning the data recording process, such as a target temperature for the temperature control of the fixing unit, is determined in accordance with a code defining the thickness of the recording sheet (for example, refer to Japanese Patent Laid-Open No. 6-348095).

The above-described data recording device first requires the thickness of the recording sheet to be inputted by operating an external unit or a switch. This operation is too complicated to be carried out by all users.

Furthermore, if a wrong code is inputted by a user, the data recording device records data in accordance with the wrong code and often causes damage to the device. As a result, significant losses, such as an increase in the downtime of the device and repairing cost, arise.

More specifically, if the data recording device is set for recording on a thin recording sheet but a thick recording sheet is used for the actual recording, the thick recording sheet will be delivered to the photoreceptor and fixing unit at a speed faster than normal. As a result, the impact of the recording sheet entering the photoreceptor and fixing unit may damage the data recording device.

Even if a wrong setting does not cause damage to the data recording device, the wrong setting may cause unsuccessful delivery and unsuccessful fixing of the recording sheet. This may cause jamming of the recording sheet that leads to unsuccessful data recording. As a result, the user will be significantly inconvenienced.

Recently, recycled paper has been in heavy use. In addition to recycled paper, various needs of users have led to the introduction of coated paper having coated surfaces and Leathac and embossed paper having surfaces with many irregularities. Such different types of special recording paper are characterized by their thickness and surface roughness.

Conditions and settings of the data recording process, including fixing and transferring processes, and conditions of mechanical control, such as sheet delivery, must be changed in accordance with the surface roughness of the recording sheet. For this reason, it has become even more important to categorize recording sheets according to the type of material the recording sheet is made of.

Inputting data recording conditions through a user interface or a hard switch, as described above, requires complicated operations that can easily lead to incorrect input.

SUMMARY OF THE INVENTION

The present invention is directed to a sheet-type detection device that easily enables a user to specify the thickness and surface roughness of a recording sheet and a method for controlling the device.

The present invention also provides a sheet-type detection device that accurately detects the thickness and the surface roughness of a recording sheet and a method for controlling the device.

In one aspect of the present invention, a sheet-type device includes a line sensor detecting light from a recording sheet, the line sensor including a first detection region and a second detection region having higher directivity than that of the first detection region; each of the first and second detection regions include a light-receiving element; and a determining unit determining a thickness of the recording sheet based on an output from the light-receiving element of the first detection region, and determining a surface roughness of the recording sheet based on an output from the light-receiving element of the second detection region.

Further features and advantages of the present invention will become apparent from the following description of exemplary embodiments (with reference to the attached drawings).

BRIEF DESCRIPTION OF THE DRAWINGS

FIGS. 4A-D illustrate a reading sensor of a sheet-type detection device according to the first embodiment of the present invention with and without built-in light-receiving lenses.

FIGS. 5A-B illustrate examples of raw data actually obtained from light-receiving units of a sheet-type detection device according to the first embodiment of the present invention.

FIG. 14 illustrates an example of the results of actually categorizing recording sheets by a sheet-type detection device according to the first embodiment of the present invention.

FIGS. 15A to 15C are tables showing sheet categories, types of recording sheets, and image-forming conditions corresponding to the thickness and the surface irregularity of recording sheets for a sheet-type detection device according to the first embodiment of the present invention.

FIGS. 18A-B are block diagrams illustrating data transfer by a reading sensor of a known sheet-type detection device.

DESCRIPTION OF THE EMBODIMENTS

First Embodiment

Before describing embodiments of the present invention, a typical data transfer process carried out by a reading sensor of a known sheet-type detection device will be described with reference to FIG. 18.

FIGS. 18A-B are block diagrams illustrating data transfer by a reading sensor of a known sheet-type detection device.

FIGS. 18A and 18B illustrate output units 1700, which are emitter followers of the reading sensor, first chips (Chip-1) 1701, second chips (Chip-2) 1702, third chips (Chip-3) 1703, and nth chips (Chip-n) 170n. The chips 1701 to 170n each include a light-receiving unit 1705 and a shift resistor 1706 for synchronizing the clock (CLK). The drawings also illustrate beams of outside light 1707, operational clock signals (CLK) 1708, and loading signals 1709. In addition, the reading sensor includes a power source VCC input, a ground (GND) terminal, and light-emitting diodes (LEDs). FIG. 18B also illustrates a selector 1710 and a selector signal 1711.

A data transfer process carried out by a known reading sensor will be described with reference to FIG. 18A.

Light energy received at the light-receiving units 1705 is converted into analog data (electric potential). The loading signals 1709 inputted from outside trigger the loading of the analog data into the shift resistors 1706. The shift resistors 1706 shift the loaded data toward the output unit 1700 in synchronization with the CLK 1708. The output value from the shift resistor 1706 of the first chip 1701 becomes the input signal to the shift resistor 1706 of the adjacent second chip 1702. Usually, this shifting process continues until all items of data are transferred to the emitter follower circuit (output unit 1700).

A data transfer process for a known reading sensor capable of increasing the detection speed when the light-receiving units to be used for detection are specified will be described with reference to FIG. 18B.

The light energy received by the light-receiving units 1705 is converted into analog data (electric potential). The loading signal 1709 inputted from outside triggers the loading of the analog data into the shift resistor 1706. The shift resistors 1706 shift the loaded data toward the output unit 1700 in synchronization with the CLK 1708. The chips 1701 to 170n are connected to the selector 1710. The chips specified to be used for detection are selected in accordance with the selector signal 1711 sent from a controlling unit. The data of the selected chips is sent to the emitter follower circuit (output unit 1700). Unless the selector signal 1711 is changed, data is outputted from the same selected chips and is outputted repeatedly. Detection of an area that extends over two chips can be easily carried out by controlling the switching of the selector signal 1711.

A reading sensor for a known sheet-type detection device will be described with reference to FIG. 19.

Figure 19:
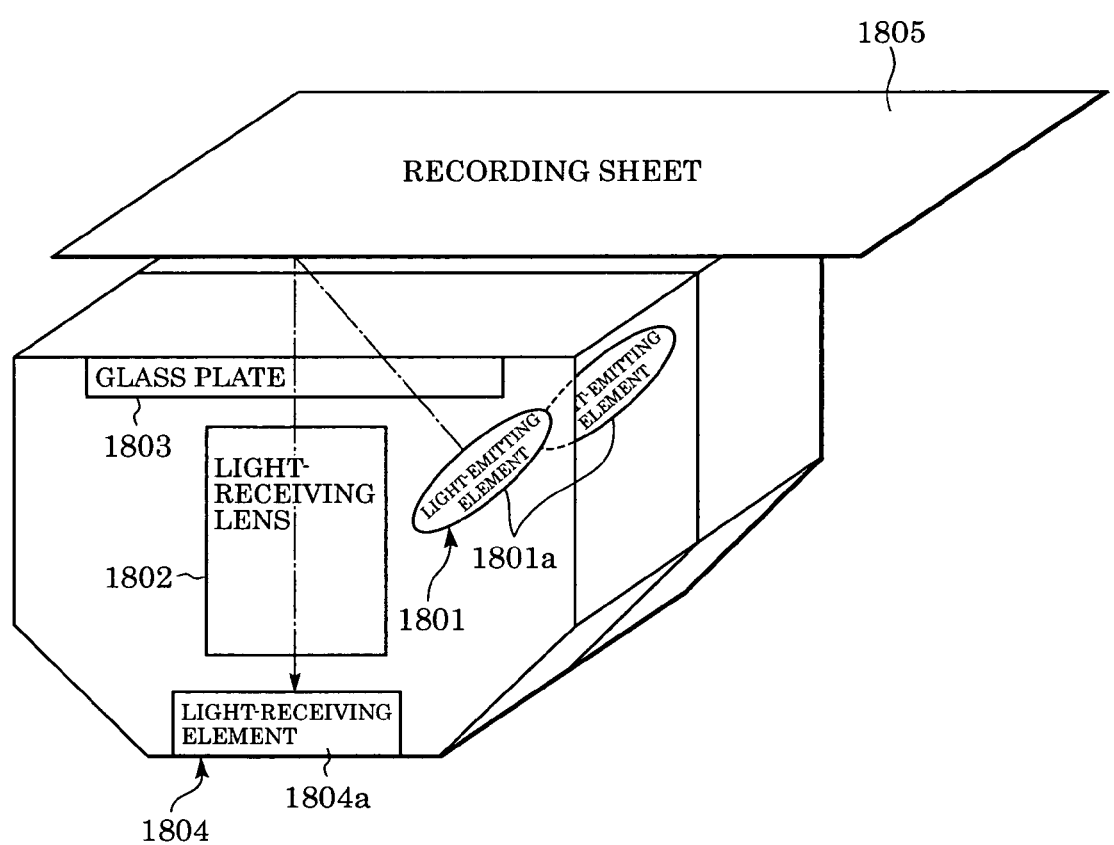
FIG. 19 is a perspective view of the structure of a reading sensor of a known sheet-type detection device.

FIG. 19 is a perspective view of a reading sensor of a known sheet-type detection device. The reading sensor includes light-emitting units 1801 including a plurality of light-emitting elements 1801a. The reading sensor also includes a light-receiving lens 1802, a glass plate 1803, and a light-receiving unit 1804 including a plurality of light-receiving elements 1804a. A recording sheet 1805 is the object to be detected by the reading sensor.

In FIG. 19, the light-emitting elements 1801a of the light-emitting units 1801 emit light to the recording sheet 1805. Then, the light reflected from the recording sheet 1805 is received by the light-receiving elements 1804a of the light-receiving units 1804 via the light-receiving lens 1802. In other words, the condition of the recording sheet 1805 is detected by using the light-emitting units 1801 disposed inside the reading sensor.

Since the method for data transfer by the reading sensor illustrated in FIG. 18 is also employed in reading sensors according to embodiments of the present invention, FIG. 18 will be referred to as necessary.

Now, details of the sheet-type detection device according to embodiments of the present invention will be described with reference to the drawings.

First Embodiment

A sheet-type detection device according to a first embodiment of the present invention will be described with reference to FIGS. 1 to 16.

Figure 1:
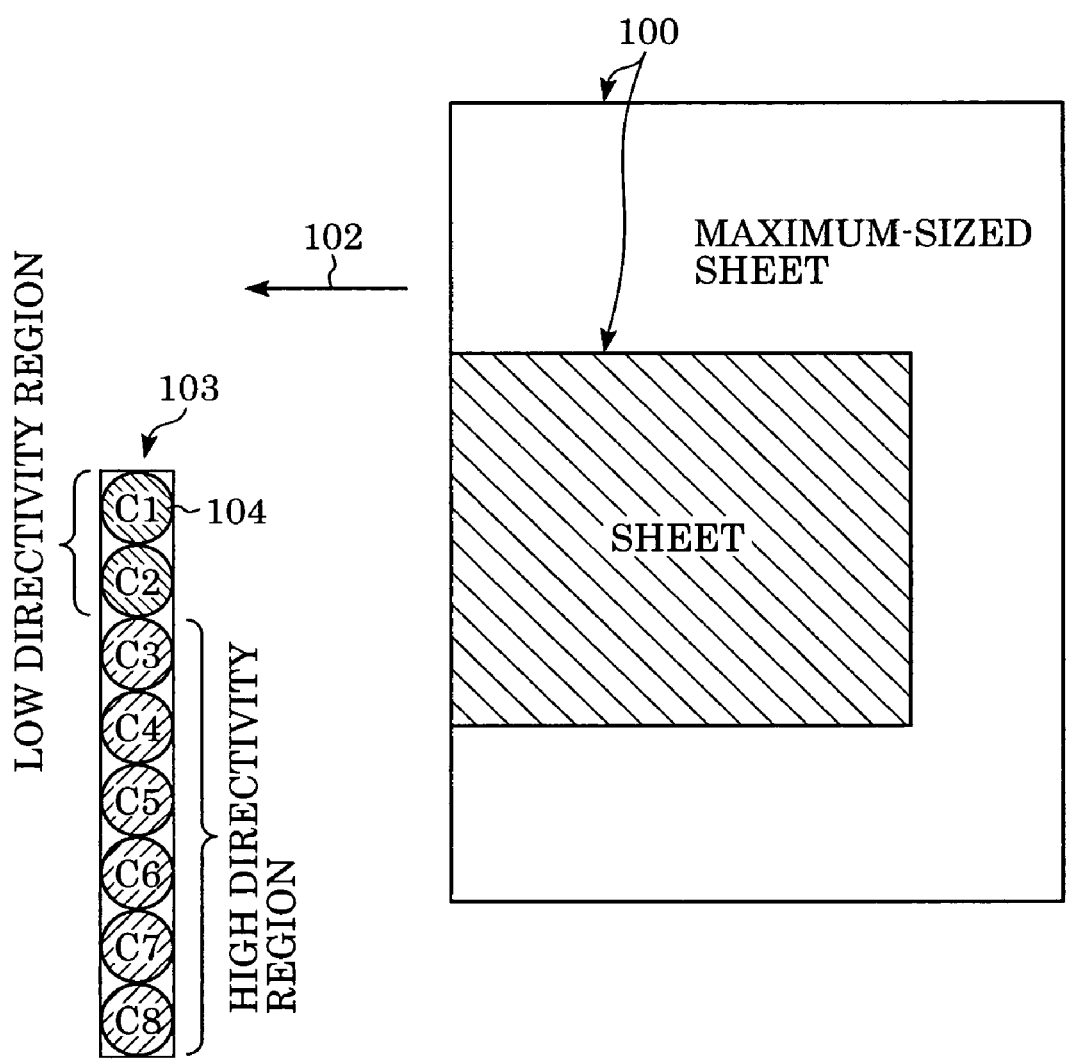
FIG. 1 illustrates the operation of a reading sensor that is a detection unit of an image-forming apparatus employing a sheet-type detection device and a information recording apparatus according to a first embodiment of the present invention.

FIG. 1 illustrates operation of the sheet-type detection device according to the first embodiment of the present invention. In FIG. 1, the maximum and minimum sizes of a recording sheet 100 that can be used for an image-forming apparatus according to this embodiment are illustrated. The recording sheet 100 is delivered in the direction indicated by Arrow 102 along a delivery line inside the image-forming apparatus. A reading sensor 103, which is a detection unit, detects the thickness and the surface irregularity (roughness) of the recording sheet 100. The reading sensor 103 includes an array of photoelectric elements (line sensor), such as a contact image sensor (CIS). The reading sensor 103 includes a chip unit 104 (according to the first embodiment, the chip unit 140 includes eight chips). Chips C1 to C8 constitute the chip unit 104. As illustrated in FIG. 18, the chips C1 to C8 each include a light-receiving unit and a shift resistor.

The reading sensor 103 includes a plurality of light-emitting elements and light-receiving elements (line sensor). The plurality of light-receiving elements is capable of scanning at once a plurality of regions on the recording sheet 100. The light-emitting elements include various types of light-emitting diodes (LEDs) having various directivities.

As described below, the light-emitting elements disposed inside the reading sensor 103 are not used. Instead, other external light-emitting elements, disposed outside the reading sensor 103, are paired with the light-receiving elements to function as a reading sensor.

The chips C1 to C8 in the reading sensor 103 of the image-forming apparatus are divided into two groups covering two different detection regions. The sensitivity of the light-receiving elements of the chips in one detection region is reduced by not providing light-receiving lens, as described below. In other words, the directivity of the chips in this region is reduced. The sensitivity of the light-receiving elements of the chips in the other detection region is increased by providing light-receiving lenses. In this way, the thickness and the surface irregularity of the recording sheet 100 can be detected using a single reading sensor 103.

The chips C1 to C8 are divided into two detection regions so that, when scanning a minimum-sized recording sheet 100, the chips C1 to C8 cover both a region for detecting the thickness of the recording sheet 100 and a region for detecting the surface irregularity of the recording sheet 100.

For example, in FIG. 1, the first chip C1 and/or the second chip C2 make up a first detection region for scanning the recording sheet 100 to detect the thickness and the chips C3 to C8 make up a second detection region for scanning the recording sheet 100 to detect the surface irregularity.

The first and second detection regions are determined based on the number of pixels including each of the chips C1 to C8 and the size of the individual chips C1 to C8. Since the detection region that does not include light-receiving lenses is predetermined, a thickness detection mode and a surface irregularity detection mode are switched at a predetermined timing after the beginning of scanning for detection.

Figure 2:
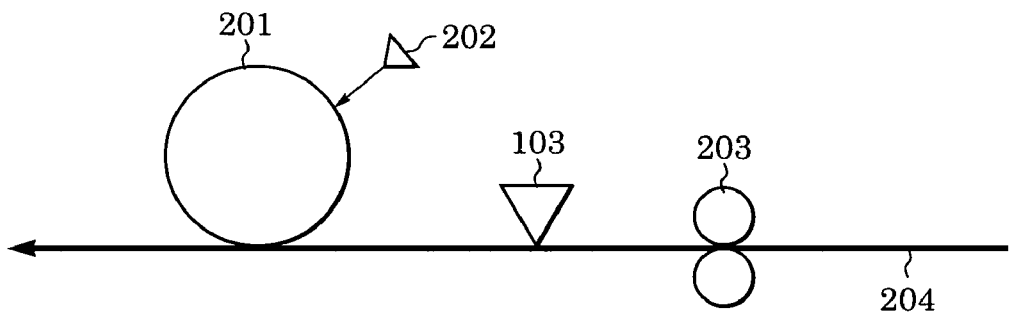
FIG. 2 illustrates the structure of the periphery of a reading sensor of an image-forming apparatus employing a sheet-type detection device and a information recording apparatus according to the first embodiment of the present invention.

FIG. 2 illustrates the peripheral area of the reading sensor 103 of the image-forming apparatus employing the sheet-type detection device and the information recording apparatus (image-forming unit) according to the first embodiment of the present invention. The components that are the same as FIG. 1 are represented by the same reference numerals.

FIG. 2 illustrates the reading sensor 103, shown in FIG. 1, a photoreceptive drum (photoreceptor, i.e., recording and processing unit) 201, and a laser device 202 for forming a latent image on the photoreceptive drum 201, recording sheet delivery rollers 203, and a recording sheet delivery path 204.

The reading sensor 103 according the first embodiment of the present invention is disposed upstream of the photoreceptive drum 201, as illustrated in FIG. 2. The reading sensor 103, however, may instead be disposed upstream of the recording sheet delivery rollers 203 (towards the right in FIG. 2).

Figure 16:
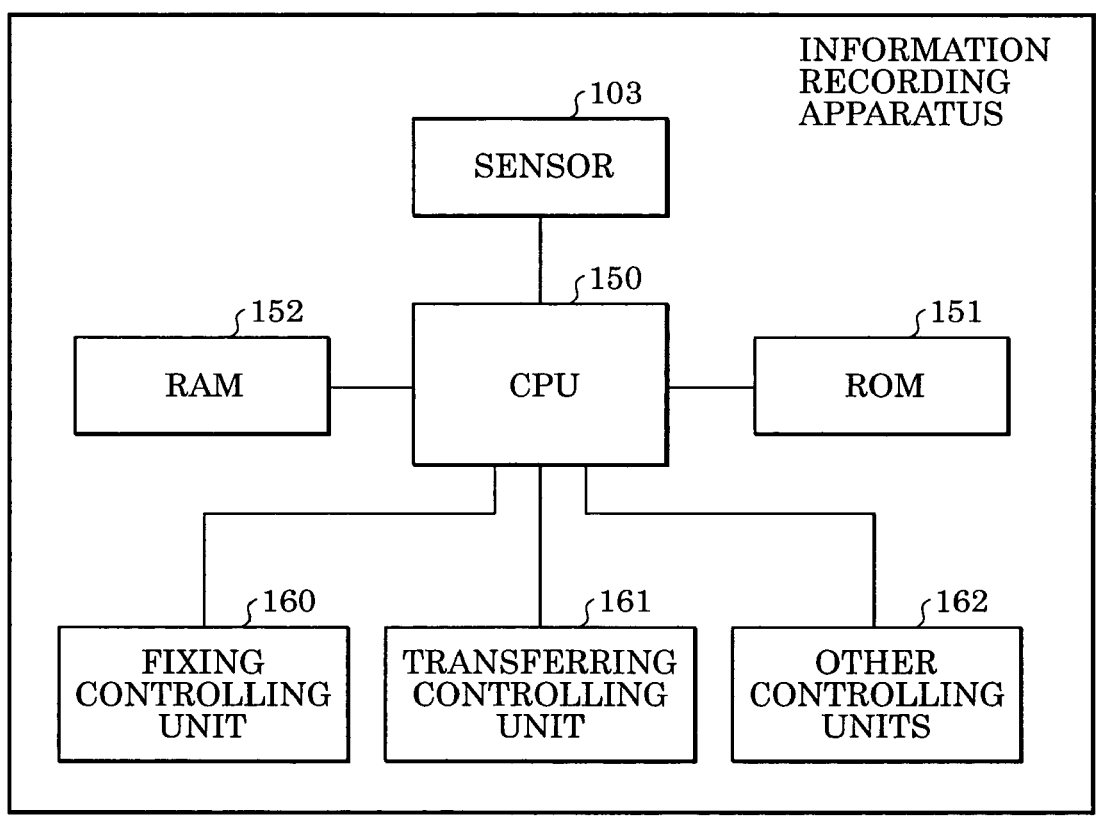
FIG. 16 is a block diagram illustrating the structure of a sheet-type detection device according to the first embodiment of the present invention.

FIG. 16 is a block diagram illustrating the overall structure of the information recording apparatus. FIG. 16 illustrates a central processing unit (CPU) 150 for controlling the entire information recording apparatus, a read-only memory (ROM) 151 for storing threshold data for determining which sheet category ( ) a recording sheet falls into and control data corresponding to the sheet category (the sheet category is described below), a random access memory (RAM) 152 functioning as a work area of the CPU 150, a fixing controlling unit 160 for controlling a fixing unit, a transferring controlling unit 161 for controlling a transferring unit, and other controlling units 162 for controlling the delivery of recording sheets, the driving of the photoreceptor, and operation of other units.

Figure 3:
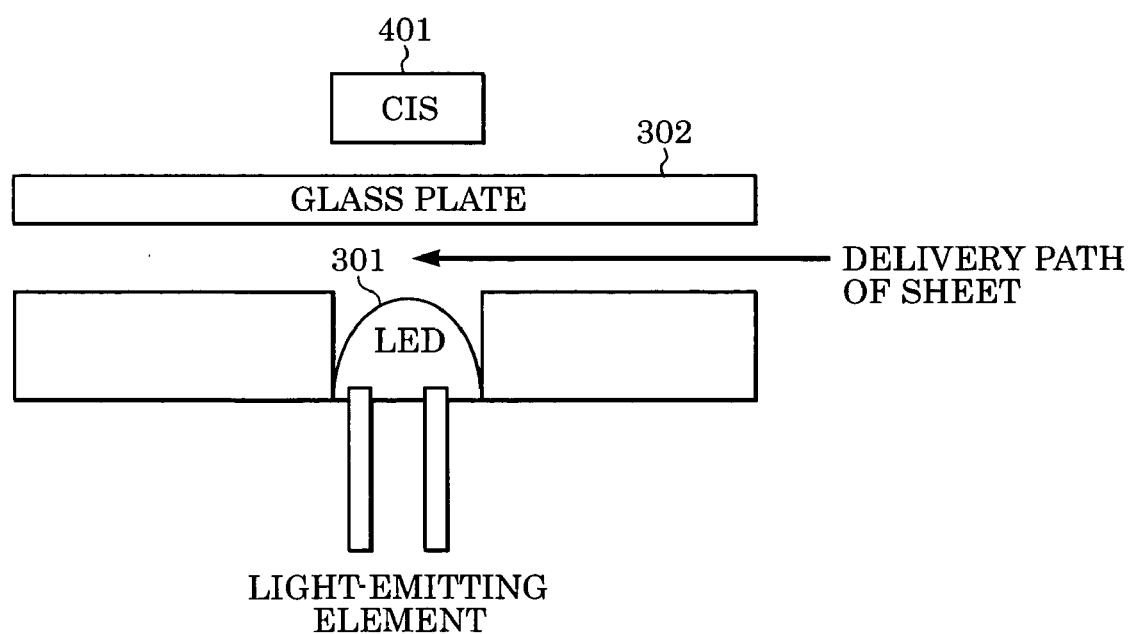
FIG. 3 illustrates the positions of a light-emitting element and a light-receiving element of a reading sensor of an image-forming apparatus employing a sheet-type detection device and a information recording apparatus according to the first embodiment of the present invention.

FIG. 3 illustrates the positions of a light-emitting element and an external light-receiving element of the reading sensor 103 according to the first embodiment of the present invention. FIG. 3 illustrates a light-receiving unit 401, which, according to this embodiment, is a CIS disposed inside the reading sensor 103, a light-emitting element, which, according to this embodiment, is a light-emitting diode (LED) 301, and a glass plate 302. The glass plate 302 prevents the recording sheet 100 from flapping while passing through the reading sensor 103 and also guards against paper dust from the recording sheet 100 and other dust from contaminating the light-receiving unit 401. The light-receiving unit 401 opposes the LED 301, and the glass plate 302 is interposed between the light-receiving unit 401 and the LED 301.

According to a known method for operating a reading sensor, illustrated in FIG. 19, the light-emitting units 1801 emit light to the recording sheet 1805, and then the light reflected at the recording sheet 1805 is received by the light-receiving units 1804 via the light-receiving lenses 1802. According to this embodiment, as illustrated in FIG. 3, the light-emitting units disposed inside the reading sensor 103 are not used. In other words, the reading sensor 103 is only used as a light-receiving device. More specifically, the external LED 301 is disposed in a position opposing the reading sensor 103 although the reading sensor 103 includes light-emitting elements. In this way, light from the external LED 301 is transmitted through the recording sheet 100 and is received by the light-receiving unit 401 of the reading sensor 103.

Accordingly, information that cannot be obtained only by reflected light or, in other words, data on the damping of the transmitted light from the recording sheet 100 is obtained. As a result, both the thickness and the surface irregularity of the recording sheet 100 are obtained by using the same reading sensor 103.

Next, the reason why the light-receiving sensitivity changes significantly depending on whether or not light-receiving lenses are provided in the reading sensor 103 is explained below with reference to FIG. 4.

FIG. 4A illustrates the positions of the chips disposed inside the reading sensor 103 according to this embodiment. The first and second chips C1 and C2 form a region with low directivity and the third to eighth chips C3 to C8 form a region with high directivity.

FIG. 4B illustrates the positional relationships of one of the LED 301, which is the light-emitting element of the reading sensor 103, the recording sheet 100, the glass plate 302, and the light-receiving unit 401. The components that are the same as in FIGS. 1 and 3 are represented by the same reference numerals. The light-receiving unit 401, including a plurality of light-receiving elements 401a, is disposed inside the reading sensor 103. In FIG. 4B, the right end of the light-receiving unit 401 is the side of the first chip C1 and the left end is the side of the eighth chip C8. The LED 301 opposes the reading sensor 103. The recording sheet 100 is delivered between the LED 301 and the glass plate 302. To detect the transmittance of the recording sheet 100, the plurality of light-receiving elements 401a making up the light-receiving unit 401 are aligned in front of the glass plate 302.

The length of the light-emitting region of the LED 301 is several millimeters, whereas the length of the light-receiving region of the light-receiving unit 401 of the reading sensor 103 is about 42 μm (according to this embodiment, the reading resolution is 600 dpi, whereas the reading resolution for a typical reading sensor is 300 to 1,200 dpi). In this way, the light from the LED 301 is detected by many light-receiving elements 401a. As a result, the detectable regions become relatively small. To increase the detectable region, a plurality of LEDs 301 may be used or the directivity of the LED 301 may be changed.

FIG. 4C illustrates part of the light-receiving unit 401 of the reading sensor 103 including light-receiving lenses. The components that are the same as in FIGS. 1 and 3 are represented by the same reference numerals.

FIG. 4C illustrates light-receiving lenses 402 opposing the light-emitting elements 401a and light beams 403 emitted from the LED 301.

The light beams 403 from the LED 301 received by the light-emitting elements 401a are focused by the light-receiving lenses 402. In this way, for example, if the resolution of the reading sensor 103 is 600 dpi, light can be detected at a high resolution of 600 dpi. The region having these light-receiving lenses 402 is the detection region with high directivity according to this embodiment.

FIG. 4D illustrates the reading sensor 103 including the light-receiving units 401 that do not have light-receiving lenses. The components that are the same as in FIGS. 1 and 3 are represented by the same reference numerals.

As illustrated in FIG. 4D, light beams 404 from the LED 301 are not focused since light-receiving lenses are not provided. The unfocused light beams 404 are received by the light-receiving elements 401a. As a result, the light beams 404 are detected at low resolution. The region without the light-receiving lenses is the detection region with low directivity according to this embodiment.

FIGS. 5A and 5B illustrate examples of raw data obtained from the light-receiving units 401, illustrated in FIGS. 4B and 4C, respectively. In FIGS. 5A and 5B, the horizontal axis represents time, or in other words, the scanning motion in the direction parallel to the axial direction of the photoreceptive drum 201 (refer to FIG. 2). The vertical axis represents the light-receiving level, or in other words, the wave shape of the signal outputted from the output unit 1700, shown in FIG. 18. FIGS. 5A and 5B are the results detected when Leathac paper, which has a high level of surface irregularity, is used as the recording sheet 100.

FIG. 5A illustrates data detected at the detection region with high directivity (i.e., the third to eighth chips C3 to C8 having high directivity).

FIG. 5B illustrates data detected at the detection region with low directivity (i.e., the first and second chips C1 and C2 having low directivity).

FIG. 5B shows almost no fluctuation in the signal level, whereas FIG. 5A shows significant fluctuations in the signal level. Since the same sheet of Leathac paper was detected in this case, two sets of data showing apparently different characteristics have been obtained by the reading sensor 103 having the structures illustrated in FIGS. 4B and 4C.

The signal level shown in FIG. 5A directly represents the surface irregularity (roughness) of the recording sheet 100. The type of the recording sheet 100, such as Leathac paper, embossed paper, or recycled paper, can be determined from this data.

Since the signal level of FIG. 5B is substantially averaged, the magnitude of the signal level of the transmitted light indicates the thickness of the recording sheet 100. The thickness of the recording sheet 100 can be determined by the value of the signal level.

Figure 6:
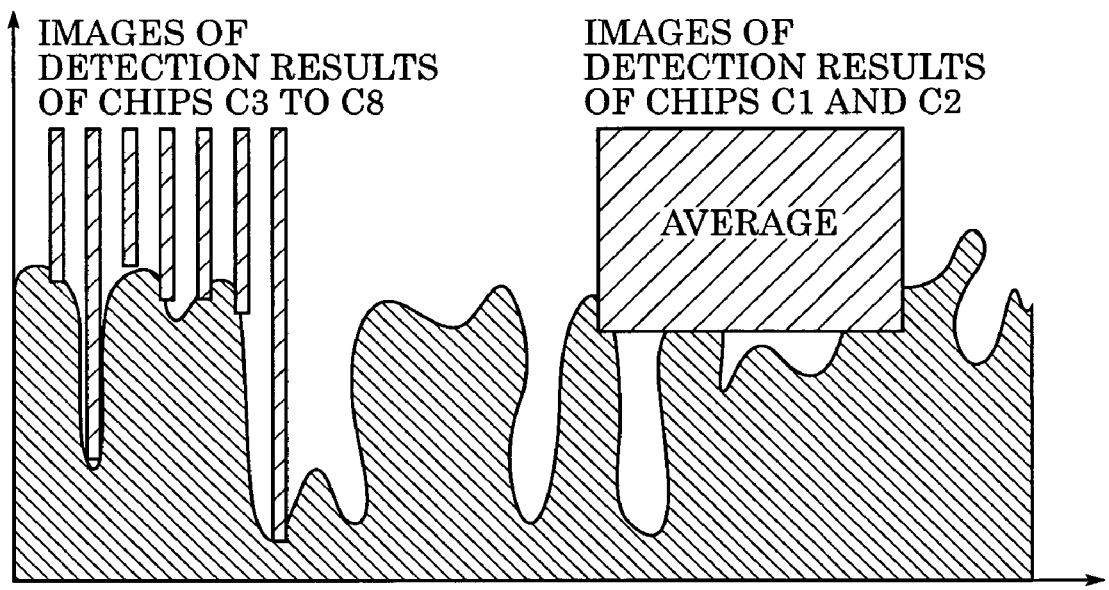
FIG. 6 illustrates images of chips of the sheet-type detection device according to the first embodiment of the present invention.

FIG. 6 illustrates the detection results of the chips C1 to C8 of the sheet-type detection device according to the first embodiment of the present invention.

As described above, both the thickness and surface irregularities of the recording sheet 100 can be detected by the reading sensor 103. As illustrated in FIGS. 15A-C, by preparing a data table that defines the relationship between the detection results and the thickness and surface irregularity of the recording sheet 100, the types of recording sheet can be divided into four categories: Sheet category 1 having a medium or high level of surface irregularity and a medium or low level of thickness; Sheet category 2 having a high level of surface irregularity and a medium or low level of thickness; Sheet category 3 having a medium or low level of surface irregularity and a high level of thickness; Sheet category 4 having a high level of surface irregularity and a high level of thickness. Here, four categories were defined. However, if necessary, more categories may be defined based on more detailed values of the thickness and surface irregularity of the recording sheet 100.

The method for determining the sheet category of the recording sheet 100 is described with reference to FIGS. 7 to 13.

FIGS. 7 to 12 are flow charts showing the method for determining the sheet category of the recording sheet 100. FIG. 13 illustrates data on the surface of different types of recording sheets. The processes shown in the flow charts of FIGS. 7 to 12 are carried out in accordance with a program stored in the ROM 151 and executed by the CPU 150.

Figure 7:
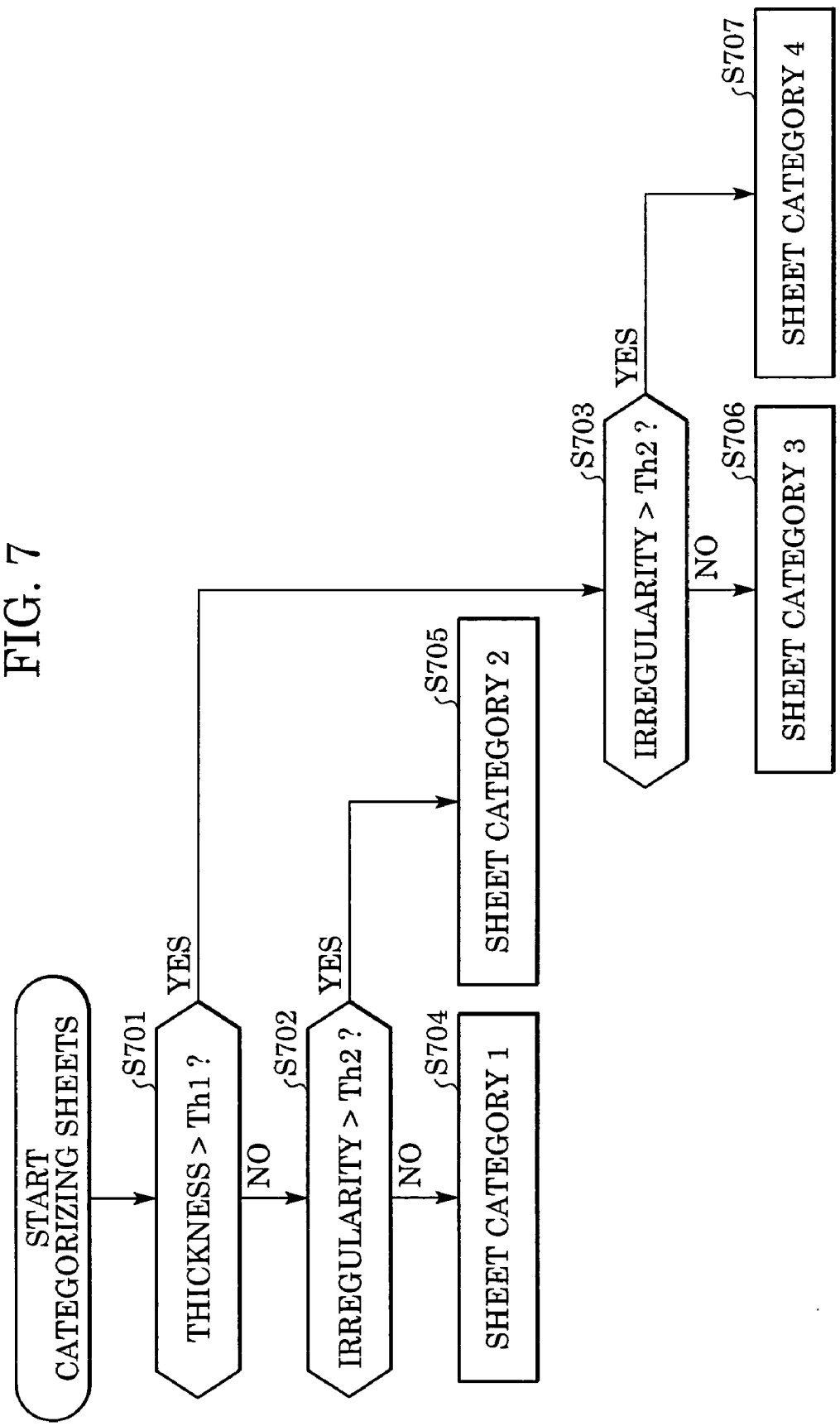
FIG. 7 is a flow chart illustrating the process of determining a sheet category by a sheet-type detection device according to the first embodiment of the present invention.

FIG. 7 is a flow chart illustrating the process for determining which sheet category the recording sheet 100 falls into.

In Step S701 of FIG. 7, it is determined whether or not the thickness of the delivered recording sheet 100 is greater than a thickness threshold value Th1 based on the data from the first and second chips C1 and C2. In this case, the data was obtained at a low resolution and thus the data is equivalent to averaged data. However, to eliminate accidental noise, it is determined whether or not the thickness is greater than the thickness threshold value Th1 based on the average of a plurality data sets per unit area.

The thickness threshold value Th1 for determining whether or not the recording sheet 100 is thick or thin is predetermined. The thickness threshold value Th1 is determined for each information recording apparatus in accordance with the processing speed and the fixing and transferring capability of the apparatus. The thickness threshold value Th1 may also be changed in accordance with the environment of the information recording apparatus to achieve the best categorization result. The best categorization result is achieved in this way because the recording speed and the mechanism for fixing and transferring may differ for each information recording apparatus and thus the thickness of a recording sheet that tends to cause unsatisfactory fixing and/or transferring may differ, such as 150 g/m$^2$ or 200 g/m$^2$. Similarly, the thickness of a recording sheet that tends to cause unsatisfactory transferring changes depending on the environment, such as humidity and/or temperature. Therefore, a fixed or variable thickness threshold value Th1, whichever is more preferable, should be selected depending on the type of information recording apparatus or the environment.

The recording sheet 100 is categorized according to the level of its surface irregularity (roughness) in Step S702 and the subsequent steps are carried out based on the results of Step S701. The process of determining the level of surface irregularity of the recording sheet 100 is described in detail below with reference to FIGS. 8 to 10.

If, in Step S701, the thickness of the recording sheet 100 is determined to be greater than the thickness threshold value Th1, the process proceeds to Step S702. If, on the other hand, the thickness of the recording sheet 100 is determined to be smaller than the thickness threshold value Th1, the process proceeds to Step S703.

In Step S702, it is determined whether or not the value of the surface irregularities of the recording sheet 100 is greater than a surface irregularity threshold value Th2. If the value of the surface irregularity of the recording sheet 100 is smaller than the surface irregularity threshold value Th2, the process proceeds to Step S704 and the recording sheet 100 is classified as Sheet category 1. If the value of the surface irregularity of the recording sheet 100 is greater than the surface irregularity threshold value Th2 in Step S702, the process proceeds to Step S705 and the recording sheet 100 is classified as Sheet category 2.

Also in Step S703, it is determined whether or not the value of surface irregularity of the recording sheet 100 is greater than the surface irregularity threshold value Th2. If the value of surface irregularity of the recording sheet 100 is smaller than the surface irregularity threshold value Th2, the process proceeds to Step S706 and the recording sheet 100 is classified as Sheet category 3. If the value of surface irregularity of the recording sheet 100 is greater than the surface irregularity threshold value Th2 in Step S703, the process proceeds to Step S707 and the recording sheet 100 is classified as Sheet category 4.

The process for determining the value of surface irregularity of the recording sheet 100 will be described with reference to FIGS. 8 to 10.

A first process for determining the value of surface irregularity of the recording sheet 100 is described with reference to FIG. 8.

Figure 8:
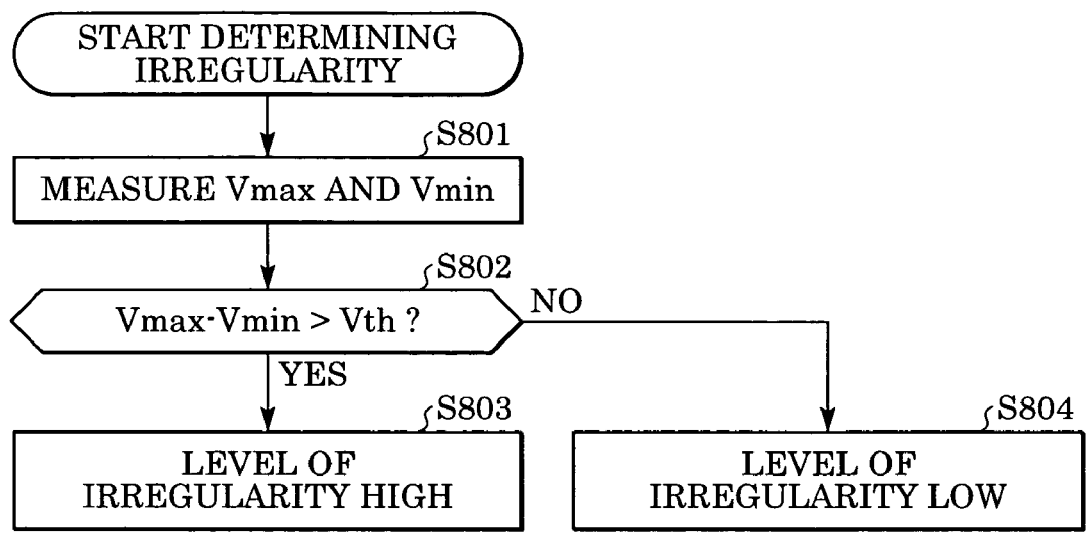
FIG. 8 is a flow chart illustrating a first process of determining the surface irregularity of a recording sheet by a sheet-type detection device according to the first embodiment of the present invention.

In Step S801 of FIG. 8, among the output data from the output unit 1700 (refer to FIG. 18), the maximum value Vmax and the minimum value Vmin of the output data corresponding to the detection region covered by the third to eighth chips C3 to C8 or a predetermined detection region covered by predetermined chips are determined. Next, in Step S802, (Vmax−Vmin) is calculated, and it is determined whether or not the calculated difference is greater than a predetermined threshold value Vth. The threshold value Vth may be a fixed value or a variable depending on the type of data-processing device because of the same reason described above.

If, in Step S802, (Vmax−Vmin) is determined to be greater than the threshold value Vth, the process proceeds to Step S803 and the level of surface irregularity of the recording sheet 100 is determined to be high. If (Vmax−Vmin) is determined not to be greater than the threshold value Vth, the process proceeds to Step S804 and the level of surface irregularity of the recording sheet 100 is determined to be low.

According to the first method for determining the level of surface irregularity of the recording sheet 100, illustrated in FIG. 8, the depth of the surface irregularity of the recording sheet 100 is determined. The number of threshold values may be increased to increase the number of classifications for the level of surface irregularity.

A second process for determining the level of surface irregularity of the recording sheet 100 is described with reference to FIG. 9.

Figure 9:
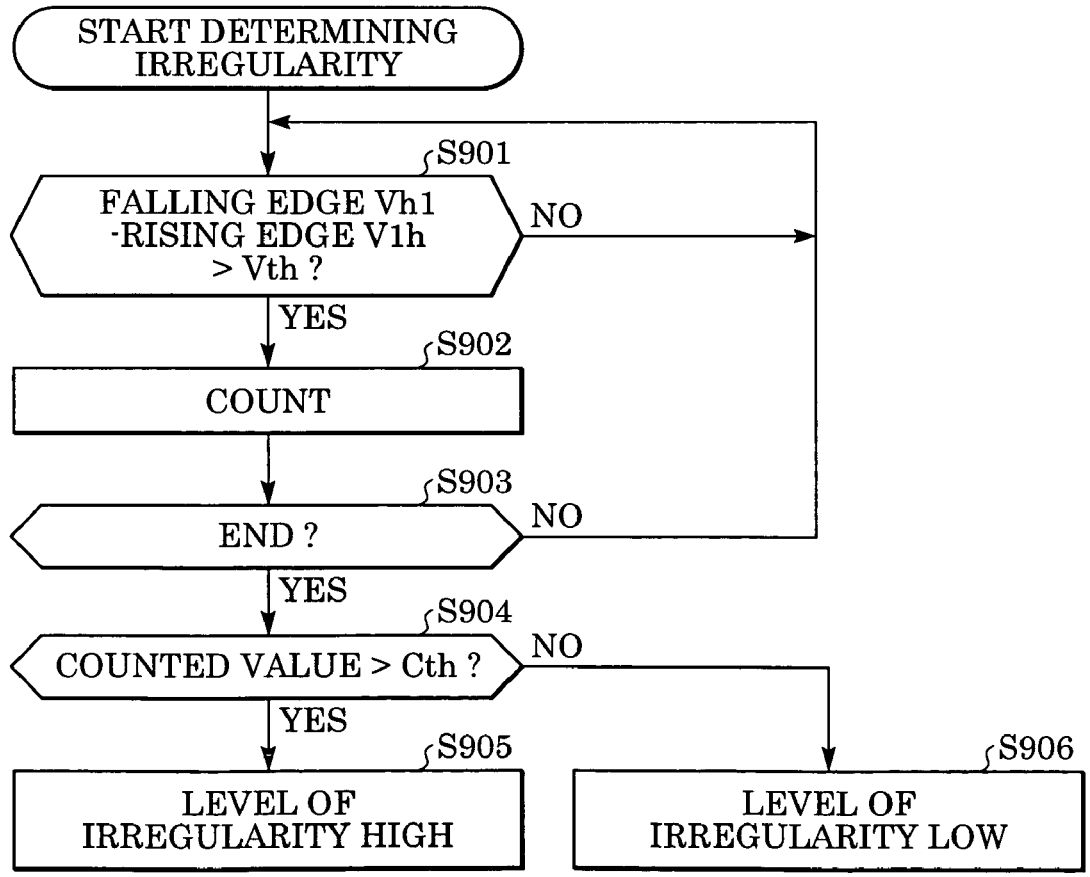
FIG. 9 is a flow chart illustrating a second process of determining the surface irregularity of a recording sheet by a sheet-type detection device according to the first embodiment of the present invention.

In Step S901 of FIG. 9, Vh1−V1$h$ is calculated, where Vh1 is the value of a falling edge and V1$h$ is the value of a rising edge of a sensor output, as illustrated in FIG. 13. In Step S901, it is determined whether or not Vh1−V1$h$ is greater than a predetermined difference threshold value Va1. This step is repeated until Vh1−V1$h$ becomes greater than the predetermined difference threshold value Va1 (i.e., Vh1−V1H>Va1). When Vh1−V1H>Va1 is satisfied, the process proceeds to Step S902. In Step S902, a counter (not shown in the drawings) for determining the value of surface irregularity is incremented by one and then the values of the falling edge Vh1 and the rising edge V1$h$ are reset to obtained the values of the falling edge Vh1 and the rising edge V1$h$ for the subsequent value of surface irregularity obtained through a subsequent detection. Then, the process proceeds to Step S903.

In Step S903, it is determined whether or not a predetermined length of the recording sheet 100 has been detected. If the predetermined length of the recording sheet 100 has been scanned, the process proceeds to Step S904. In Step S904, the count value and a predetermined count threshold value Cth is compared to determine whether or not the count value is greater than the count threshold value Cth. If the count value is determined to be greater than the count threshold value Cth, the process proceeds to Step S905 and the level of surface irregularity of the recording sheet 100 is determined to be high. If, in Step S904, the count value is determined not to be greater than the count threshold value Cth, the process proceeds to Step S906 and the level of surface irregularity of the recording sheet 100 is determined to be low. If Vh1−V1$h$>Va1 is not satisfied for a predetermined amount of time after the beginning of the process, the level of surface irregularity is determined to be low.

In this case, the difference threshold value Va1 and the count threshold value Cth may also be a fixed value or a variable depending on the type of data-processing device for the same reason described above. The number of count threshold values may be increased to increase the number of classifications for the level of surface irregularity.

The frequency of large irregularities to appear on the surface of the recording sheet 100 can be determined by the second process for determining the level of surface irregularity of the recording sheet 100, illustrated in FIG. 9.

A third process for determining the level of surface irregularity of the recording sheet 100 is described with reference to FIG. 10.

Figure 10:
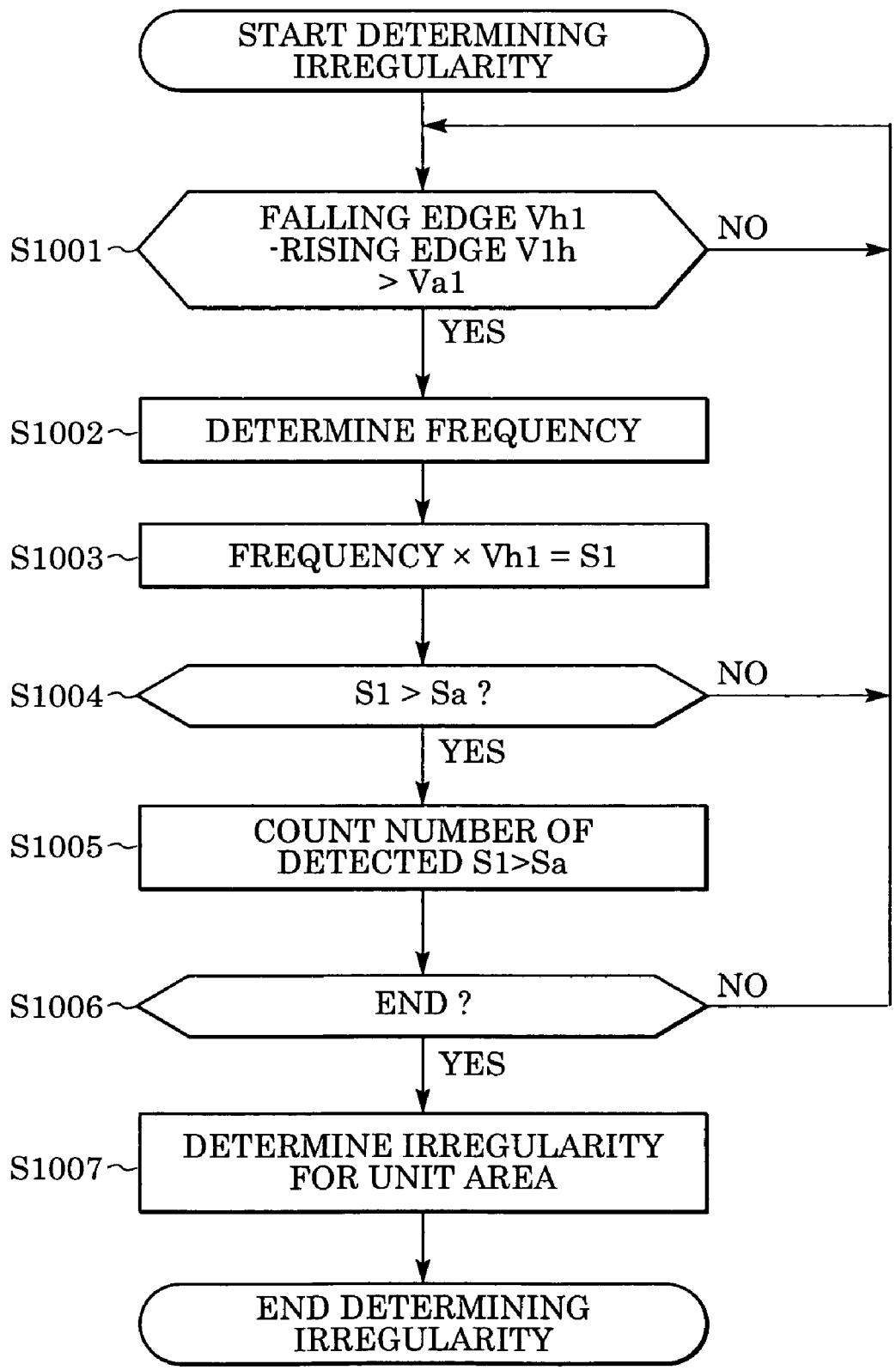
FIG. 10 is a flow chart illustrating a third process of determining the surface irregularity of a recording sheet by a sheet-type detection device according to the first embodiment of the present invention.

In Step S1001 in FIG. 10, Vh1−V1$h$ is calculated, where Vh1 is the value of a falling edge and V1$h$ is the value of a rising edge of a sensor output, as illustrated in FIG. 13. Also, it is determined whether or not Vh1−V1$h$ is greater than a predetermined difference threshold value Va1. This step is repeated until Vh1−V1$h$ becomes greater than the predetermined difference threshold value Va1 (i.e., Vh1−V1$h$>Va1). When Vh1−V1$h$>Va1 is satisfied, the process proceeds to Step S1002. In Step S1002, the time from the moment the falling edge Vh1 is detected to the time the rising edge V1$h$ is detected or, i.e., the frequency f is determined.

Figure 13A:
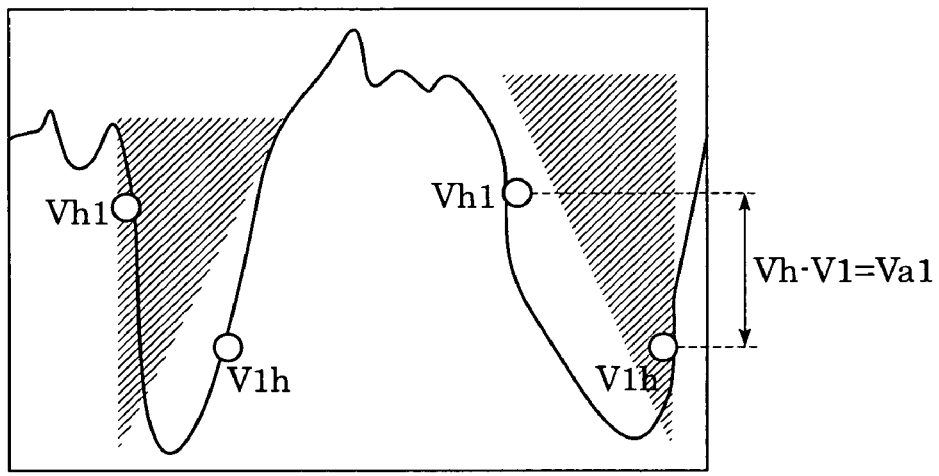
FIGS. 13A-C illustrate the surface of a recording sheet of the sheet-type detection device according to the first embodiment of the present invention.
Figure 13B:
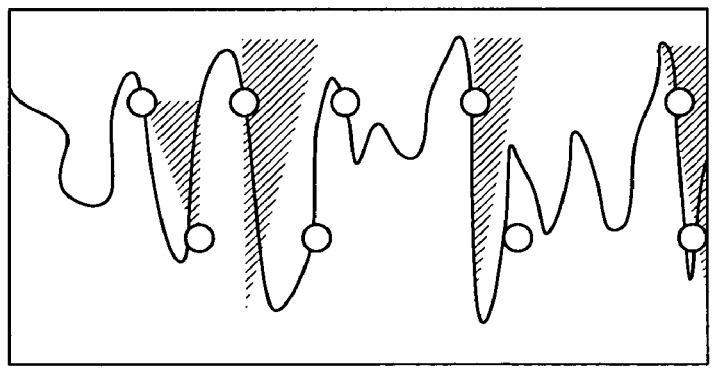

The process proceeds to Step S1003 to calculate the product of the frequency f determined in Step S1002 and the height of the falling edge Vh1 to obtain an area S1, as illustrated in FIGS. 13A and 13B. According to this embodiment, [½× frequency f×(Vmax−Vmin)] is calculated to obtain the area of a pseudo-triangle.

Then in Step S1004, it is determined whether or not the area S1 calculated in Step S1003 is greater than a predetermined area threshold value Sa. If the area S1 is determined not to be greater than the area threshold value Sa, the process returns to Step S1001. If the area S1 is determined to be greater than the area threshold value Sa, the process proceeds to Step S1005. In Step S1005, the number of times the area S1 was determined to be greater than the area threshold value Sa is counted and the values of the falling edge Vh1 and the rising edge V1$h$ are reset to obtain the values of the falling edge Vh1 and the rising edge V1$h$ for the value of the surface irregularity obtained through a subsequent detection. Then, in Step S1006, it is determined whether or not a predetermined length of the recording sheet 100 has been detected. If the predetermined length of the recording sheet 100 has been scanned, the process proceeds to Step S1007. In Step S1007, the level of surface irregularity of the recording sheet 100 per unit area is determined based on the counted values. Then, the process is ended. If Vh1−V1$h$>Va1 is not satisfied within a predetermined amount of time after the start of the process, the process forcefully proceeds to Step S1002.

In this case, the difference threshold value Va1 and the area threshold value Sa may also be fixed values or variable values depending on the type of data-processing device. The number of difference threshold values and area threshold values may be increased to increase the number of classifications for the level of surface irregularity.

The depth and frequency of the surface irregularity of the recording sheet 100 can be determined by the third process for determining the level of surface irregularity of the recording sheet 100, as illustrated in FIG. 10.

For example, by carrying out one or a combination of the three methods for detecting the level of surface irregularity, the level of surface irregularity of the recording sheet 100 can be detected accurately and the type of the recording sheet 100 can be determined.

Figure 13C:
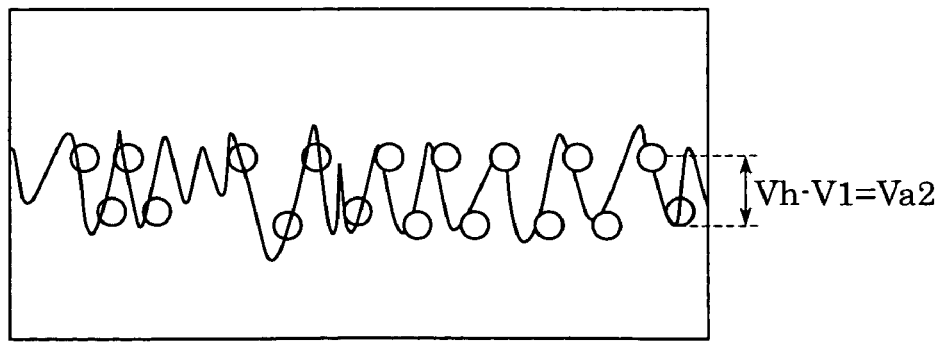

FIGS. 13A, 13B, and 13C illustrate the measurements of the surface irregularity of the recording sheet 100 that are obtained by carrying out the processes shown in the flow charts of FIGS. 8 to 10. FIG. 13A illustrates the measurements of the surface irregularity of Leathac paper. The surface irregularity of Leathac paper extends over a large area and occurs at a low frequency. FIG. 13B illustrates the measurements of the surface irregularity of embossed paper. The surface irregularity of embossed paper extends over a small area and occurs at a low frequency. FIG. 13C illustrates the measurements of the surface irregularity of recycled paper. The level of surface irregularity of recycled paper is low (i.e., Vh1−V1$h$ is small) and the frequency of the surface irregularity is high. In this case, it is effective to carry out the detection with the difference threshold value Va2 being reduced.

Subsequently, the process of scanning by the reading sensor 103, detecting the type of recording sheet 100, and controlling the image-forming conditions will be described with reference to the flow chart illustrated in FIGS. 11 and 12.

Figure 11:
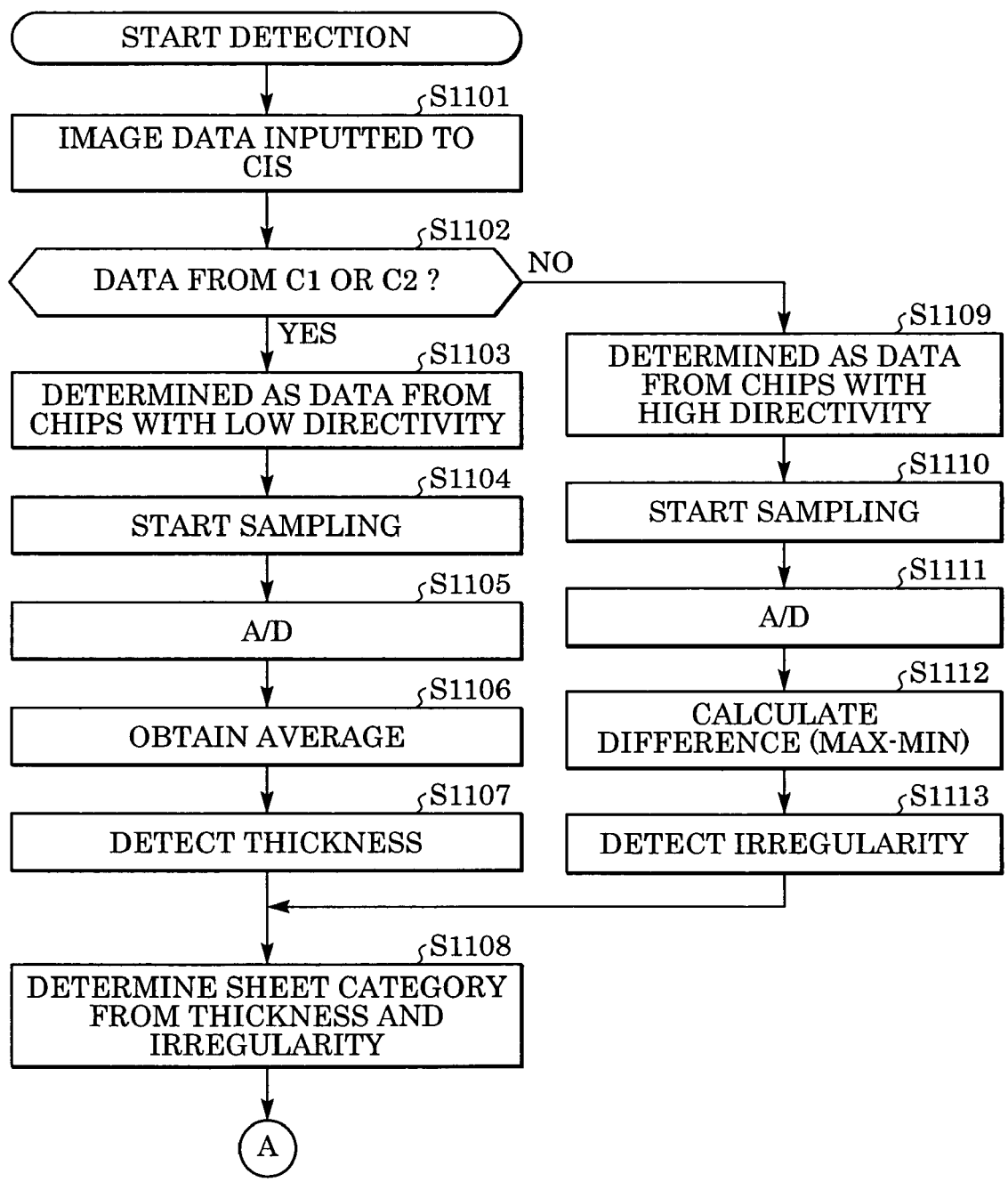
FIG. 11 is a flow chart illustrating a process of detecting the surface irregularity and the thickness of a recording sheet by the sheet-type detection device according to the first embodiment of the present invention.

As illustrated in FIG. 11, in Step S1101, image data is inputted to the chips of the reading sensor (CIS) 103. Subsequently, in Step S1102, it is determined whether or not the image data inputted in Step S1101 is from the first chip C1 and/or the second chip C2 (therefore, alternatively from the third to eighth chips C3 to C8) based on the selector signal 1711 and/or the input timing. If the image data is determined to be from the first chip C1 and/or the second chip C2, the process proceeds to Step S1103. In Step S1103, the image data is determined to be data from the detection region having low directivity. Then, the process proceeds to Step S1104 to start sampling image data. Subsequently, in Step S1105, the image data sampled in Step S1104 is converted into a digital signal by an analog/digital (A/D) converter.

In Step S1105, the image data converted into digital data is used for determining the level of the surface irregularity of the recording sheet 100, as illustrated in FIGS. 8 to 10.

In Step S1106, the image data converted into digital data in Step S1105 is used to calculate the average of the output values. Then in Step S1107, the thickness of the recording sheet 100 is determined based on the result of the calculation carried out in Step S1106. Then, the process proceeds to Step S1108.

If, in Step S1102, the image data is determined not to be from the first chip C1 and/or second chip C2, the process proceeds to Step S1109 and the image data is determined to be data from the detection region having high directivity. Then, in Step S1110, image data sampling is started. Then, in Step S1111, the image data sampled in Step S1110 is converted into a digital signal by an A/D converter. Subsequently, in Step S1112, image data converted into digital data in Step S1111 is used to calculate, for example, Vmax-Vmin of the output data. Then, in Step S1113, the level of surface irregularity, i.e., the depth of the surface irregularity of the recording sheet 100, is determined from the difference calculated in Step S1112. Then, the process proceeds to Step S1108.

In Step S1108, the thickness and the surface irregularity of the recording sheet 100 are determined from the results of Steps S1107 and S1113. Finally, the recording sheet 100 is classified into one of the categories shown in FIGS. 7 and 15A. Then, the process proceeds to the steps shown in FIG. 12.

Figure 12:
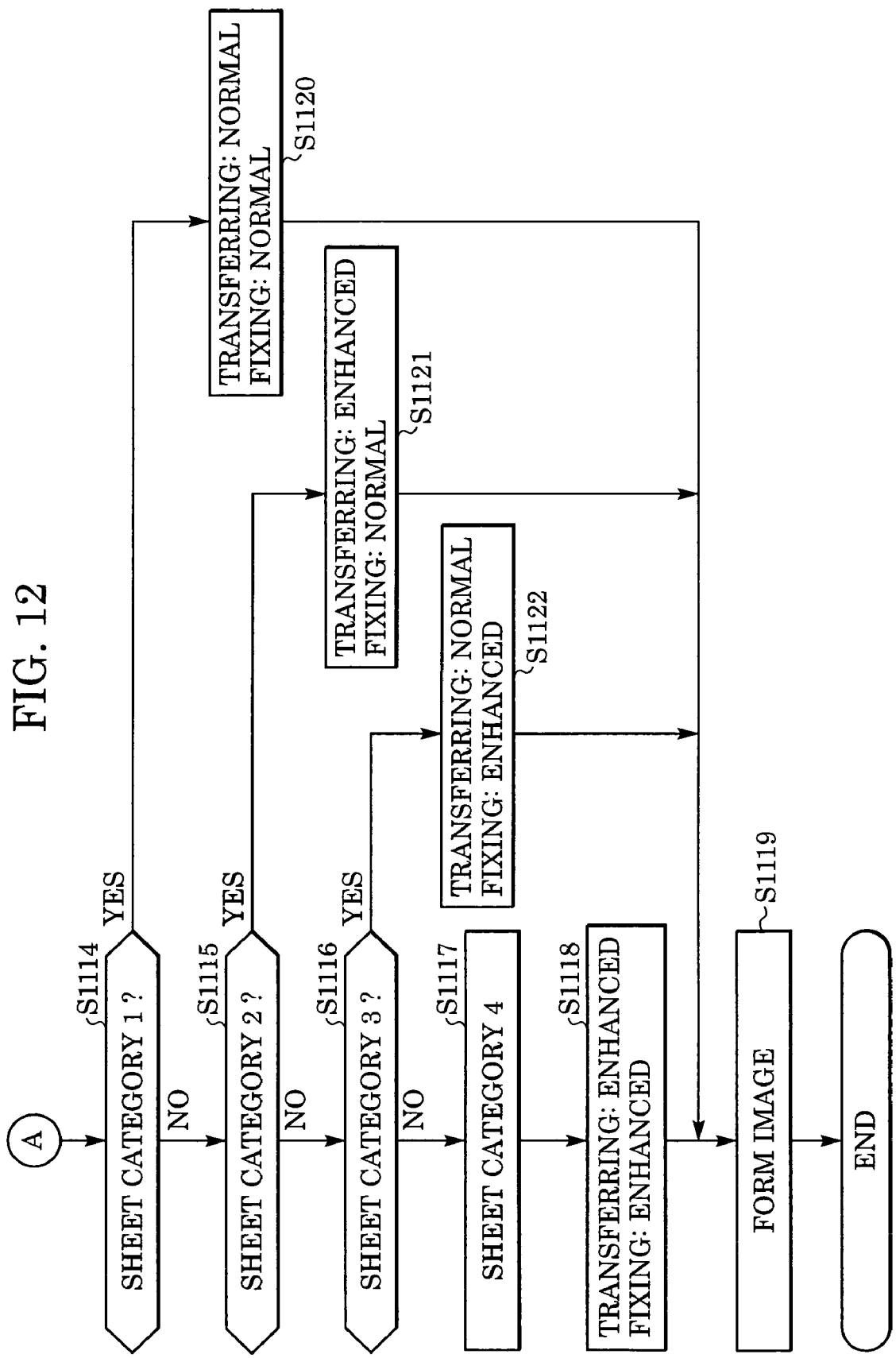
FIG. 12 is a flow chart illustrating a process of detecting the surface irregularity and the thickness of a recording sheet by a sheet-type detection device according to the first embodiment of the present invention.

In Step S1114, as shown in FIG. 12, it is determined whether or not the sheet category for the recording sheet 100 determined in Step S1108, shown in FIG. 11, is Sheet category 1. The recording sheet 100 determined to be Sheet category 1 has characteristics such that the level of surface irregularity is low and the level of thickness is low. This recording sheet 100 is determined to be regular paper in accordance with FIG. 15B. Then, the process proceeds to Step S1120. In Step S1120, the conditions for the transferring controlling unit 161 and the fixing controlling unit 160 are set such that transferring and fixing are both controlled in a normal mode. Then, the process proceeds to Step S1119.

If, in Step S1114, the recording sheet 100 is determined not to be Sheet category 1, the process proceeds to Step S1115. In Step S1115, it is determined whether or not the recording sheet 100 falls into Sheet category 2. The recording sheet 100 determined to be Sheet category 2 has characteristics such that the level of surface irregularity is high and the level of thickness is low. This recording sheet 100 is determined to be recycled paper in accordance with FIG. 15B. Since images do not transfer well onto recycled paper, the transferring pressure must be increased. Accordingly, in Step S1121, the conditions for the transferring controlling unit 161 and the fixing controlling unit 160 are set such that transferring and fixing are controlled in an enhanced mode and a normal mode, respectively. Then, the process proceeds to Step S1119.

If, in Step S1115, the recording sheet 100 is determined not to be Sheet category 2, the process proceeds to Step S1116. In Step S1116, it is determined whether or not the recording sheet 100 falls into Sheet category 3. The recording sheet 100 determined to be Sheet category 3 has characteristics such that the level of irregularity is low and the level of thickness is high. This recording sheet 100 is determined to be coated paper in accordance with FIG. 15B. Since images do not fix well onto coated paper, fixing must be improved by increasing the fixing temperature, reducing the fixing speed, and/or increasing the holding pressure applied to the recording sheet 100. Accordingly, in Step S1122, the conditions for the transferring controlling unit 161 and the fixing controlling unit 160 are set such that transferring and fixing are controlled in a normal mode and an enhanced mode, respectively. Then, the process proceeds to Step S1119.

If, in Step S1116, the recording sheet 100 is determined not to be Sheet category 3, the process proceeds to Step S1117. In Step S1117, the recording sheet 100 is determined to be Sheet category 4. A sheet category 4 recording sheet 100 has characteristics such that the level of surface irregularity is high and the level of thickness is high. This recording sheet 100 is determined to be Leathac or embossed paper in accordance with FIG. 15B. Since images do not fix well to Leathac and embossed paper, fixing must be improved by increasing the fixing temperature, reducing the fixing speed, and/or increasing the holding pressure applied to the recording sheet 100. Furthermore, since images do not transfer well onto Leathac and embossed paper, the transferring pressure must be increased. Accordingly, in Step S1118, the conditions for the transferring controlling unit 161 and the fixing controlling unit 160 are set such that both transferring and fixing are controlled in an enhanced mode. Then, the process proceeds to Step S1119.

In Step S1119, an image is formed in accordance with the conditions set above. Then, the process is ended.

As described above, by setting control conditions in accordance with the different categories of recording sheets, as illustrated in FIG. 15C, images may be formed in a manner most suitable for the thickness and surface irregularity of a recording sheet.

FIG. 14 illustrates the results of categorizing various types of recording sheets in accordance with the processes in the flow charts shown in FIGS. 7 to 12.

As shown in FIG. 14, Leathac and embossed paper have the greatest Vmax-Vmin value and have a high level of thickness. Accordingly, Leathac and embossed paper are classified as Sheet category 4. Coated paper has a high level of surface irregularity and a high level of thickness. Accordingly, coated paper is classified as Sheet category 3. Cardboard has a relatively high level of surface irregularity compared to coated paper and has a high level of thickness. Accordingly, cardboard is classified as Sheet category 3. Recycled paper has a high level of surface irregularity and a low level of thickness. Accordingly, recycled paper is classified as Sheet category 2. Regular paper has a low level of surface irregularity and a low level of thickness. Accordingly, regular paper is classified as Sheet category 1.

As described above, by using the sheet-type detection device according to the first embodiment of the present invention, the thickness and the surface irregularity of the recording sheet 100 can be detected accurately.

According to the image-forming apparatus that is a information recording apparatus according to the first embodiment of the present invention, the data-recording conditions for recording data on the recording sheet 100 can be set based on the detection results of the sheet-type detection device.

Second Embodiment

A second embodiment according to the present invention will be described below with reference to FIGS. 17A-D.

According to the above-described sheet-type detection device according to the first embodiment of the present invention, the light-emitting elements in the reading sensor 103 were not used and instead, a plurality of LEDs 301 opposing the reading sensor 103 were used as light-emitting elements. However, the light-emitting elements disposed inside the reading sensor 103 may be used instead of the external LEDs 301 for the third to eighth chips C3 to C8 that form the detection region with high directivity for detecting the level of surface irregularity of the recording sheet 100. In this case, instead of detecting the light transmitted through the recording sheet 100, the light reflected from the recording sheet 100 will be detected.

When detecting the reflected light, light-receiving lenses are disposed in positions opposing the third to eighth chips C3 to C8 in order to obtain data with high directivity.

FIGS. 17A-D illustrate a sheet-type detection device according to the second embodiment of the present invention for detecting reflected light. In FIGS. 17A-D, the components that are the same as in FIG. 4 are represented by the same reference numerals.

The sheet-type detection device illustrated in FIGS. 17A-D differs from the device illustrated in FIG. 4 in that the light-receiving units 401 corresponding to the first and second chips C1 and C2 detect light transmitted through the recording sheet 100 in the same manner as the first embodiment whereas the third to eighth chips C3 to C8 detect light reflected from the recording sheet 100.

Figure 17A:
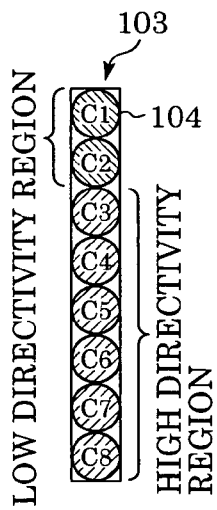
FIGS. 17A-D illustrate a reading sensor of a sheet-type detection device according to a second embodiment of the present invention with and without built-in light-receiving lenses.
Figure 17B:
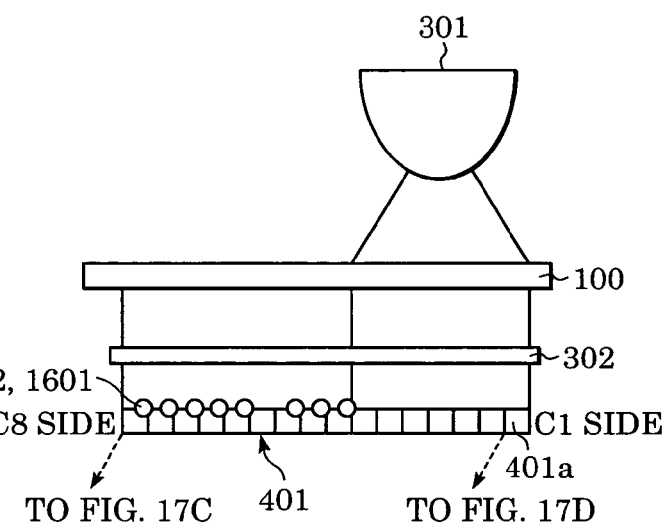

FIG. 17A illustrates the positions of the chips disposed in the reading sensor 103. Since the details of the drawing are the same as those of FIG. 4A, descriptions are omitted. FIG. 17B illustrates the positional relationships of one of the LED 301, which is the light-emitting element of the reading sensor 103, the recording sheet 100, the glass plate 302, and the light-receiving unit 401. In FIG. 17B, the components that are the same as those illustrated in FIGS. 1, 3, and 4 are represented by the same reference numerals. Unlike the first embodiment, light-receiving lenses 402 and light-receiving elements 1601 oppose light-receiving elements 401a of the light-receiving unit 401 corresponding to the third to eighth chips C3 to C8 to detect the amount of light reflected from the recording sheet 100.

Figure 17C:
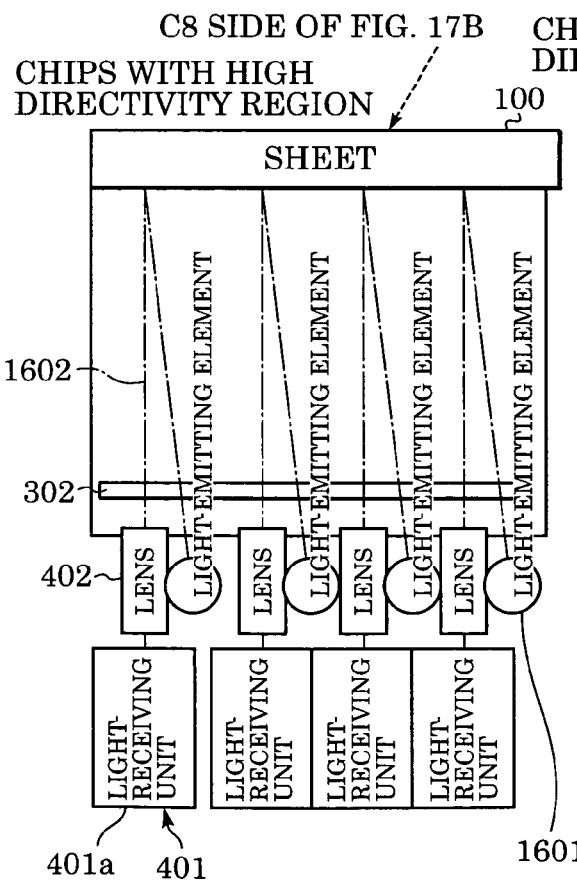

FIG. 17C is an enlarged view of a part of the reading sensor 103 including the light-receiving lenses 402. In FIG. 17C, the components that are the same as those illustrated in FIGS. 1, 3, and 4 are represented by the same reference numerals.

As illustrated in FIG. 17C, the light-receiving lenses 402 and the light-receiving elements 1601 oppose the light-receiving elements 401a of the light-receiving units 401 corresponding to the third to eighth chips C3 to C8. Beams of light 1602 are emitted from the light-emitting elements 1601 and are reflected at the recording sheet 100.

The beams of light 1602 from the light-emitting elements 1601 emitted at the recording sheet 100 are reflected at the surface of the recording sheet 100. Then, the reflected light beams 1602 are focused by the light-receiving lenses 402 and are received by the light-receiving elements 401a of the light-receiving units 401 corresponding to the third to eighth chips C3 to C8. According to this embodiment, this region is a detection region with high directivity.

Figure 17D:
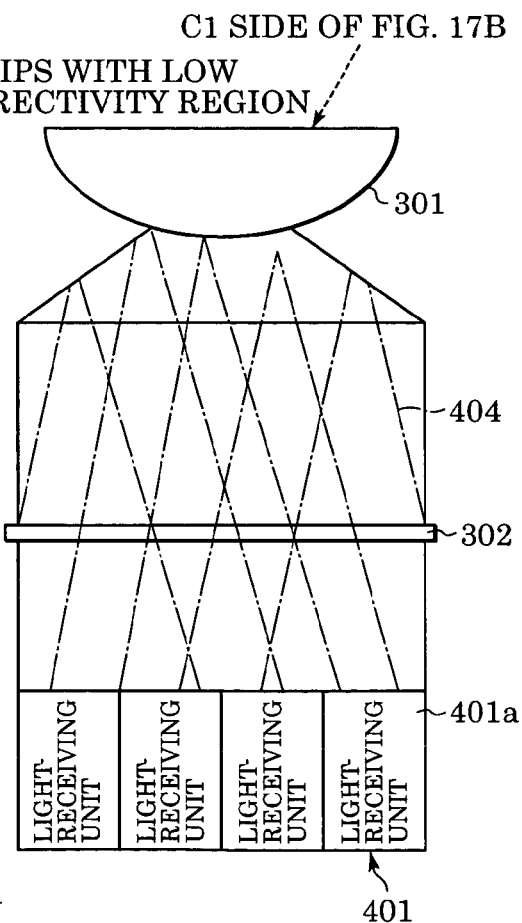

FIG. 17D illustrates part of the light-receiving units 401 corresponding to the first and second chips C1 and C2 where light-receiving lenses are not provided. Since the details of the drawing are the same as those of FIG. 4D, descriptions are omitted. According to the second embodiment of the present invention, the first and second chips C1 and C2 function as a region having low directivity.

The characteristics of the data obtained according to this embodiment are the same as the characteristics of the data obtained according to above-described first embodiment, illustrated in FIG. 5. The control and operation for detection and their advantages according to this embodiment are also the same those according to the first embodiment.

Other Embodiments

The embodiments of the present invention have been described above. However, the embodiments of the present invention are not limited to the above-described embodiments, and any structure may be included in the scope of the present invention as long as it is capable of realizing the functions according to the aspects and the embodiments of the present invention.

The sheet-type detection device according to the present invention may also be realized by supplying a storage medium storing a software program code for realizing the functions of the above-described embodiments to a system or an apparatus and reading out and executing the program code stored on the storage medium by a computer (central processing unit (CPU) or microprocessor unit (MPU)) of the system or apparatus. In such a case, the read out program code introduces a new aspect according to the present invention.

The storage medium for storing the above-mentioned program code may be, for example, a flexible disk, a hard disk, an optical disk, an magneto-optic disk, a compact disk-read only memory (CD-ROM), compact disk-recordable (CD-R), a magnetic tape, a non-volatile memory card, or a ROM.

The functions of the embodiments of the present invention are realized not only by executing a program code read out by a computer but also is realized when an operating system (OS) operating on the computer carries out the entire processing or part of the processing based on the program code.

Also, when the embodiments of the present invention are realized by carrying out the entire processing or part of the processing based on the program code read out from a storage medium is stored in a memory included in an expansion board of a computer or an expansion unit connected to a computer by a CPU included in the expansion board or expansion unit, the program code is included in the scope of the present invention.

While the present invention has been described with reference to exemplary embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

This application claims priority from Japanese Patent Application No. 2004-170296 filed Jun. 8, 2004, which is hereby incorporated by reference herein.

What is claimed is:

1. A sheet-type detection device, comprising:
 a light source configured to emit light at a recording sheet;
 a line sensor including a plurality of light-receiving elements arranged along a direction intersecting a direction to convey the recording sheet, each element of the plurality of light-receiving elements configured to detect light transmitted through the recording sheet, some of the plurality of light-receiving elements configured to function as a first detection unit, and others of the plurality of light-receiving elements configured to function as a second detection unit, the first detection unit configured to detect transmitted light being unfocused and the second detection unit configured to detect transmitted light being focused at a higher resolution than the first detection unit; and
 a determining unit configured to determine a thickness of the recording sheet based on an output from the first detection unit, and determining a surface roughness of the recording sheet based on an output from the second detection unit.

2. The sheet-type detection device according to claim 1, further comprising a lens,
 wherein the second detection unit detects the light from the recording sheet, the light being focused through the lens, and
 wherein the first detection region unit detects the light from the recording sheet, the light being unfocused without passing through the lens.

3. The sheet-type detection device according to claim 1, wherein the determining unit determines a material type of the recording sheet based on the thickness and surface roughness of the recording sheet.

4. An image-forming apparatus, comprising:
 a sheet conveying unit configured to deliver a recording sheet;
 an image-forming unit configured to form an image on the recording sheet delivered by the sheet conveying unit;
 a light source configured to emit light at a recording sheet delivered by the sheet conveying unit;
 a line sensor including a plurality of light-receiving elements arranged in a direction intersecting a direction to convey the recording sheet, each element of the plurality of light-receiving elements configured to detect light transmitted through the recording sheet, some of the plurality of light-receiving elements configured to function as a first detection unit, and others of the plurality of light-receiving elements configured to function as a second detection unit, the first detection unit configured to detect transmitted light being unfocused and the second detection unit configured to detect transmitted light being focused at a higher resolution than the first detection unit;
 a determining unit determining a thickness of the recording sheet based on an output from the first detection unit, and determining a surface roughness of the recording sheet based on an output from the second detection unit; and
 a control unit determining conditions for controlling the image-forming unit based on the thickness and surface roughness determined by the determining unit.

* * * * *